United States Patent
Doris

(10) Patent No.: US 10,016,558 B2
(45) Date of Patent: Jul. 10, 2018

(54) MEDICAL DEVICE COMPRISING A VISUAL AND AN AUDIO ALARM SIGNAL GENERATOR

(71) Applicant: Fresenius Vial SAS, Brézins (FR)

(72) Inventor: Lionel Doris, Grenoble (FR)

(73) Assignee: Fresenius Vial SAS, Brézins (FR)

( * ) Notice: Subject to any disclaimer, the term of this patent is extended or adjusted under 35 U.S.C. 154(b) by 0 days.

(21) Appl. No.: 15/546,472

(22) PCT Filed: Feb. 5, 2016

(86) PCT No.: PCT/EP2016/052468
§ 371 (c)(1),
(2) Date: Jul. 26, 2017

(87) PCT Pub. No.: WO2016/128308
PCT Pub. Date: Aug. 18, 2016

(65) Prior Publication Data
US 2018/0021513 A1    Jan. 25, 2018

(30) Foreign Application Priority Data
Feb. 11, 2015  (EP) .................................... 15305197

(51) Int. Cl.
*G08B 3/00* (2006.01)
*A61M 5/168* (2006.01)
(Continued)

(52) U.S. Cl.
CPC ........ *A61M 5/16831* (2013.01); *A61M 5/142* (2013.01); *A61M 5/172* (2013.01);
(Continued)

(58) Field of Classification Search
CPC . A61M 5/16831; A61M 2205/18; A61M 5/14
(Continued)

(56) References Cited

U.S. PATENT DOCUMENTS

| | | |
|---|---|---|
| 3,342,176 A | 9/1967 | Kaplan et al. |
| 5,103,214 A * | 4/1992 | Curran .................. G08B 29/10 340/292 |

(Continued)

FOREIGN PATENT DOCUMENTS

| | | |
|---|---|---|
| EP | 2 460 546 A1 | 6/2012 |
| WO | WO 03/053503 A1 | 7/2003 |

OTHER PUBLICATIONS

International Search Report and Written Opinion, counterpart PCT Appl. No. PCT/EP2016/052468, 10 pp. (dated Apr. 25, 2016).

*Primary Examiner* — Phung Nguyen
(74) *Attorney, Agent, or Firm* — Cook Alex Ltd.

(57) ABSTRACT

A medical device (2, 3, 20), in particular a medical infusion device (2, 3, 20), comprises a control unit (200) for controlling operation of the medical device (2, 3, 20), a visual alarm generator (201) for generating a visual alarm signal (V), and an audio alarm generator (202) for generating an audio alarm signal (S). Herein, the control unit (200) is constituted to control the visual alarm generator (201) and the audio alarm generator (202), in case of an alarm condition, for producing a visual alarm signal (V1, V2) and an audio alarm signal (S1, S2) which are offset with respect to each other by a predetermined time difference (T1). In this way a medical device is provided which allows to enhance the perception of a user to help the user to quickly identify a medical device on which an alarm condition has occurred.

13 Claims, 3 Drawing Sheets

(51) Int. Cl.
    *A61M 5/142*     (2006.01)
    *A61M 5/50*     (2006.01)
    *A61M 5/172*     (2006.01)
    *A61M 5/145*     (2006.01)

(52) U.S. Cl.
    CPC ......... *A61M 5/5086* (2013.01); *A61M 5/1452* (2013.01); *A61M 5/1684* (2013.01); *A61M 5/16827* (2013.01); *A61M 2005/16863* (2013.01); *A61M 2205/18* (2013.01); *A61M 2205/581* (2013.01); *A61M 2205/583* (2013.01)

(58) Field of Classification Search
    USPC ....... 340/309.15, 691.5, 691.1, 573.1, 815.4, 340/384.1
    See application file for complete search history.

(56) References Cited

U.S. PATENT DOCUMENTS

| | | |
|---|---|---|
| 5,239,988 A | 8/1993 | Swanson et al. |
| 2011/0050428 A1* | 3/2011 | Istoc ..................... G16H 50/20 340/573.1 |
| 2016/0135758 A1* | 5/2016 | Sabota .................. A61G 11/00 340/573.1 |

* cited by examiner

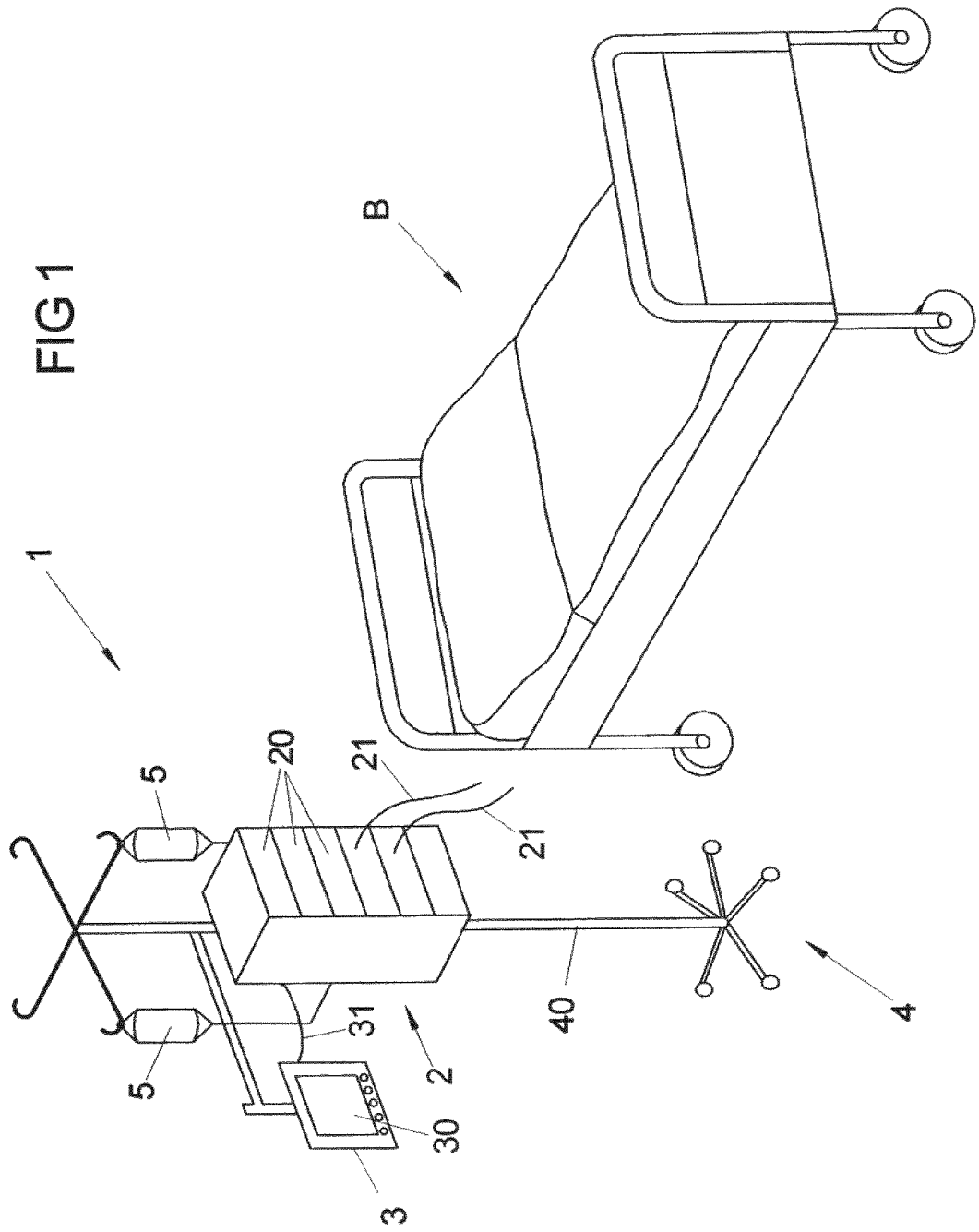

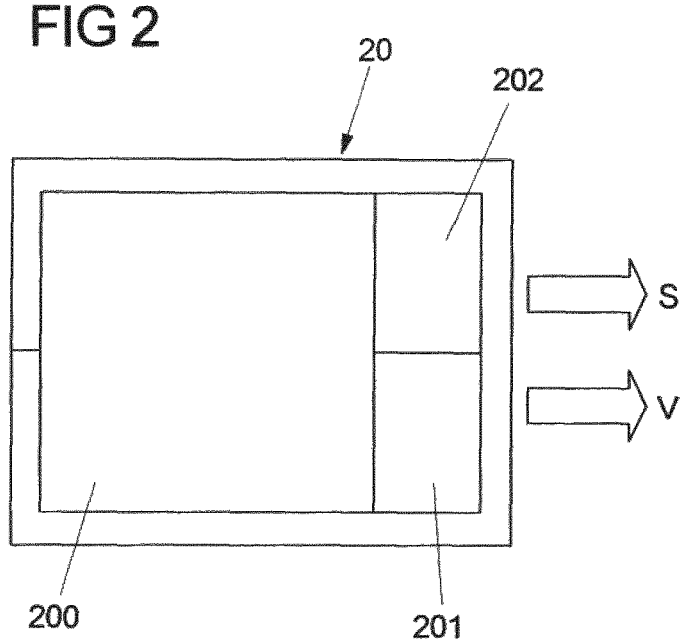
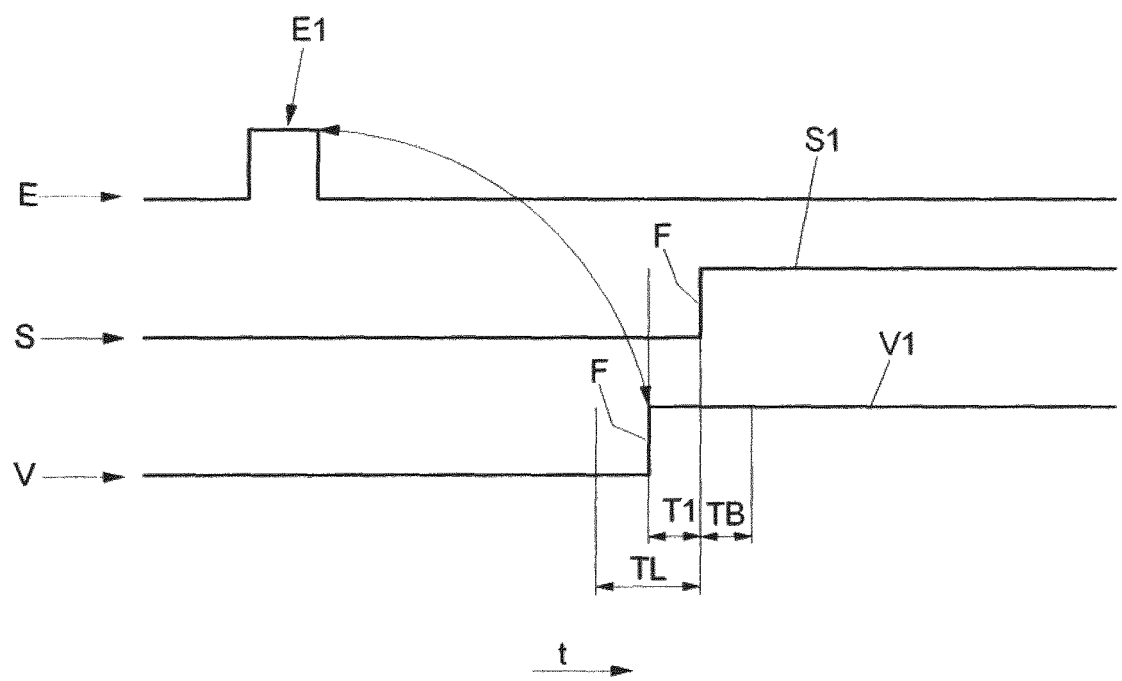

MEDICAL DEVICE COMPRISING A VISUAL AND AN AUDIO ALARM SIGNAL GENERATOR

The present application is a U.S. National Stage of PCT international Patent Application No. PCT/EP2016/052468, filed Feb. 5, 2016, which claims priority to EP Application No. 15305197.4, filed Feb. 11, 2015, both of which are hereby incorporated herein by reference.

BACKGROUND

The invention relates to a medical device, in particular a medical infusion device, and a method for controlling a medical device.

A medical device of this kind comprises a control unit for controlling operation of the medical device, a visual alarm generator for generating a visual alarm signal and an audio alarm generator for generating an audio alarm signal.

A medical device of this kind may for example be an infusion device such as an infusion pump, for example a volumetric infusion pump or a syringe infusion pump. A medical device of this kind, however, may—without limiting the scope of the invention—also be a rack for mechanically holding a multiplicity of infusion devices, or a control device such as an infusion managing device centrally connected to for example a rack for controlling the infusion operation of multiple infusion devices.

In a typical scenario, for example in a hospital environment, a multiplicity of infusion devices such as infusion pumps are arranged at the bedside of a patient for performing one or multiple infusion operations at a time for administering medical fluids such as drugs, nutrients or the like to a patient. The infusion operations are performed by the individual infusion devices, but may for example be controlled by a central control device, also called "infusion manager". For initiating one or multiple infusion operations, a nurse may for example enter control commands into the central control device, the central control device then issuing control signals for controlling one or multiple infusion devices for performing the actual infusion operation.

The correct execution of infusion operations may be vital to a patient. Hence, if a malfunction at an infusion device occurs, for example due to an occlusion in an infusion line, due to a technical malfunction of an infusion mechanism or due to a software error or the like, an alarm is issued to notify a user, for example a nurse, such that appropriate countermeasures can be taken to an ensure a correct execution of infusion operations and to prevent a possibly harmful malfunction leading to an incorrect execution of an infusion operation.

At the bedside of a patient, in particular in the presence of a large number of medical devices for example in the environment of an intensive care unit, multiple alarms may occur at a time, in addition to other noises such as a beeping of monitoring devices or the like. If an alarm occurs, it therefore may be sometimes difficult for a user to immediately and unambiguously make out where the alarm is stemming from and on which medical device a problem may be present. This may be critical because an alarm condition may require immediate attention and immediate countermeasures in order to ensure operation of a medical device.

There, hence, is a desire to enhance the perception of an alarm by a user, allowing the user to quickly identify the medical device on which an alarm condition has occurred among a multiplicity of other medical devices. In this regard it for example is known to generate audio alarm signals such as different melodies on different medical devices as so-called auditory warnings, as it is specified for example in the standard IEC 60601-1-8.

U.S. Pat. No. 5,239,988 discloses a cardio-pulmonary resuscitation aid which comprises a visual indicator means and an audible alarm generator means which are simultaneously actuated. The visual indicator may, for example, comprise a light flashing in a synchronized fashion with an audible signal provided by the audible alarm generator means.

U.S. Pat. No. 3,342,176 discloses a cardiac monitor in which an audible clicking sound synchronized with a flashing light is produced indicating the rate and rhythm of a patient's heart beat being monitored.

It is an object of the instant invention to provide a device and a method allowing to enhance the perception of a user to help the user to quickly identify a medical device on which an alarm condition has occurred.

SUMMARY

Accordingly, the control unit of the medical device is constituted to control the visual alarm generator and the audio alarm generator, in case of an alarm condition on the medical device, for producing a visual alarm signal and an audio alarm signal which are offset with respect to each other by a predetermined time difference.

The control unit, hence, is constituted to control the visual alarm generator and the audio alarm generator for producing a visual alarm signal and an audio alarm signal in a coordinated, concerted fashion. In particular, the control unit is constituted to control the visual alarm generator and the audio alarm generator such that a visual alarm signal and an audio alarm signal are produced which are offset with respect to each other by a predetermined time difference. Hence, the visual alarm signal and the audio alarm signal are not produced at the same time or at an arbitrary time with respect to each other, but are offset with respect to each other in a predefined manner.

The offset may be measured, for example, between a rising flank of the visual alarm signal and a rising flank of the audio alarm signal.

For example, the control unit may be configured to control the visual alarm generator and the audio alarm generator such that the visual alarm signal precedes the audio alarm signal by the predetermined time difference. The predetermined time difference herein preferably does not exceed 100 ms and may for example lie in the range between 5 ms and 100 ms, in particular between 20 ms and 70 ms, for example at 50 ms.

Alternatively, the control unit may be configured to control the visual alarm generator and the audio alarm generator such that the audio alarm signal precedes the visual alarm signal by the predetermined time difference. In this case, the predetermined time difference may, for example, lie in the range between 5 ms and 70 ms, in particular between 10 ms and 40 ms, for example, at 30 ms.

The audio alarm signal and the visual alarm signal, hence, are offset with respect to each other and, upon the occurrence of an alarm condition at the medical device, are initiated at different times. By this, the perception of the alarm condition at the medical device and the identification of the medical device among a multiplicity of different medical devices may be enhanced. This is based on findings in auditory-visual studies in which it has been observed that a combined neural activation of audition and vision in a human being's brain may increase the probability that at least one of those sensory events may be detected. The issuing of an audio alarm and a visual alarm in parallel, hence, may improve the perception of the alarm condition by a user. It furthermore has been found, however, that a user may not be able to attend a multiplicity of different sensory inputs at one time such that a user may not detect or localise a visual and/or audio alarm if too many sensory inputs are provided at the same time.

The instant invention now is based on the finding that the perception by a user may be improved if different sensory inputs, in the instant case a visual alarm signal and an audio alarm signal, are offset in time with respect to each other in a predefined manner.

Generally, in this regard, vision dominates audition with respect to the perception of a user and with respect to the localization. Vision, hence, provides a more reliable source of location information allowing a user to identify a source of an alarm signal. However, when auditory and visual information appear in a synchronized fashion, audio information may be captured by visual information in that a user perceives audio information to originate from the same source as the visual information.

This effect is also illustrated by the "ventriloquism effect" which refers to the tendency of a human being to perceive sounds as coming from the same location as a visual event. Within the ventriloquism effect the movement of the mouth of a ventriloquist dummy intuitively is associated with a speaking sound such that the perception of a speaking dummy arises.

This known effect is now used in a refined fashion for issuing alarm signals at a medical device. In particular, by issuing a visual alarm signal and an audio alarm signal in an offset manner having a predetermined time difference it is made sure that the user may easily perceive both alarm signals without being overwhelmed by too many sensory signals occurring at the same time, wherein the concerted generation of the alarm signals makes sure that the user perceives the visual alarm signal and the audio alarm signal as arising from the same source such that a user may easily identify the medical device from which the alarm signals stems.

It has been found that the offset between the alarm signals should not be too large. In particular, it may be beneficial if the visual alarm signal precedes the audio alarm signal by no more than 100 ms or alternatively lags behind the audio alarm signal by no more than 40 ms.

In principle, it is also possible that multiple visual alarm signals and multiple audio alarm signals are generated in a concerted fashion having predetermined time differences in-between them.

For example, in one embodiment, the control unit of the medical device may be configured to control the visual alarm generator and the audio alarm generator to produce, in case of an alarm condition, first a first audio alarm signal, then a first visual alarm signal following the first audio alarm signal by a first predetermined time difference, and then a second audio alarm signal following the first visual alarm signal by a second predetermined time difference. Hence, a first audio alarm signal is followed by a first visual alarm signal, which then again is followed by a second audio alarm signal. The time differences between the different alarm signals are predetermined and may lie, for example, in the range between 5 ms and 40 ms for the first time difference (between the first audio alarm signal and the first visual alarm signal) and in the range between 5 ms and 100 ms for the second time difference (between the first visual alarm signal and the second audio alarm signal).

In principle, more alarm signals may follow, for example a second visual alarm signal following the second audio alarm signal and so on.

Alternatively, a visual alarm signal may be generated first to precede an audio alarm signal, followed by other alarm signals. In this case, the control unit controls the visual alarm generator and the audio alarm generator to produce, in case of an alarm condition, a first visual alarm signal, followed by a first audio alarm signal occurring a first predetermined time difference after the first visual alarm signal, which then is followed by a second visual alarm signal occurring a second predetermined time difference after the first audio alarm signal. In this case, the first predetermined time difference may, for example, lie in the range between 5 ms and 100 ms, whereas the second predetermined time difference lies is the range between 5 ms and 40 ms.

In principle, the second visual alarm signal may again be followed by a second audio alarm signal, which may be followed by other alarm signals.

Multiple alarm signals, hence, are generated in a concerted fashion having predetermined time differences in-between them. Because the alarm signals are offset with respect to each other in a predetermined fashion, the perception by a user and the association of the alarm signals which each other for a user is improved, and an overwhelming occurrence of too many alarm signals at the same time is prevented.

As said, the offset between two alarm signals beneficially is measured between rising flanks of the alarm signals, i.e., between the start points of the alarm signals. The alarm signals herein beneficially last longer than the predetermined time difference such that at the occurrence of a second alarm signal following a first alarm signal by a predetermined time difference the first alarm signal is still present and hence allows for an easy and intuitive association of the alarm signal with each other.

The visual alarm generator may in principle be constituted to generate any sort of visual alarm effects. The visual alarm generator may, for example, be constituted to produce a light effect and for this may comprise a LED component, an incandescent lamp, a vacuum display tube, a CRT display device, a LCD display device and/or an OLED display device. Herein, "CRT" stands for Cathode Ray Tube, "LCD" stands for Liquid Cristal Display, "LED" stands for Light Emitting Diode and "OLED" stands for Organic Light Emitting Diode.

The visual alarm generator may, for example, produce a steady visual alarm signal. For example, a light may shine up at a medical device and may remain shining for a predetermined amount of time or until it is switched off by a user. In addition or alternatively, the visual alarm generator may also produce a time-varying visual alarm signal, such as a blinking signal. The visual signal may, for example, be any light signal, or may also be a colour signal produced by a corresponding light component or produced on a display, for example, in the shape of a red-blinking box or the like.

The audio alarm signal generator, in principle, may comprise a suitable transducer for producing an audio signal such as a piezoelectric buzzer, an electromagnetic buzzer or a loudspeaker. The audio alarm signal generator may, for example, produce a steady audio sound having a predetermined frequency characteristic, for example having a single or multiple discrete frequency components. The audio signal generator may, however, be also constituted to produce a time-varying audio alarm signal such as a melody having a specific sequence of tones or the like.

An alarm condition may be any event associated with a malfunction of the medical device or another condition which shall be indicated to a user. A malfunctioning may relate to an erroneous hardware or software operation of the medical device, or may also relate to an external malfunctioning condition, such as an occlusion in an infusion line or an empty bag detected in an infusion set connected to an infusion pump.

The object is also achieved by a method for controlling a medical device, in particular a medical infusion device, in which a control unit controls the operation of the medical device, a visual alarm generator generates a visual alarm signal, and an audio alarm generator generates an audio alarm signal. Herein, the control unit controls the visual alarm generator and the audio alarm generator such that, in case of an alarm condition, a visual alarm signal and an audio alarm signal are produced which are offset with respect to each other by a predetermined time difference.

The advantages and advantageous embodiments described above for the medical device equally apply also to the method such that it shall be referred to the above.

BRIEF DESCRIPTION OF THE DRAWINGS

The idea underlying the invention shall subsequently be described in more detail with regard to the embodiments shown in the figures. Herein:

FIG. 1 shows a schematic view of a set-up of medical devices at the bedside of a patient;

FIG. 2 shows a schematic view of a medical device;

FIG. 3 shows a diagram of time lines of a visual alarm signal and an audio alarm signal.

DETAILED DESCRIPTION OF THE EMBODIMENTS

Figure 4A:
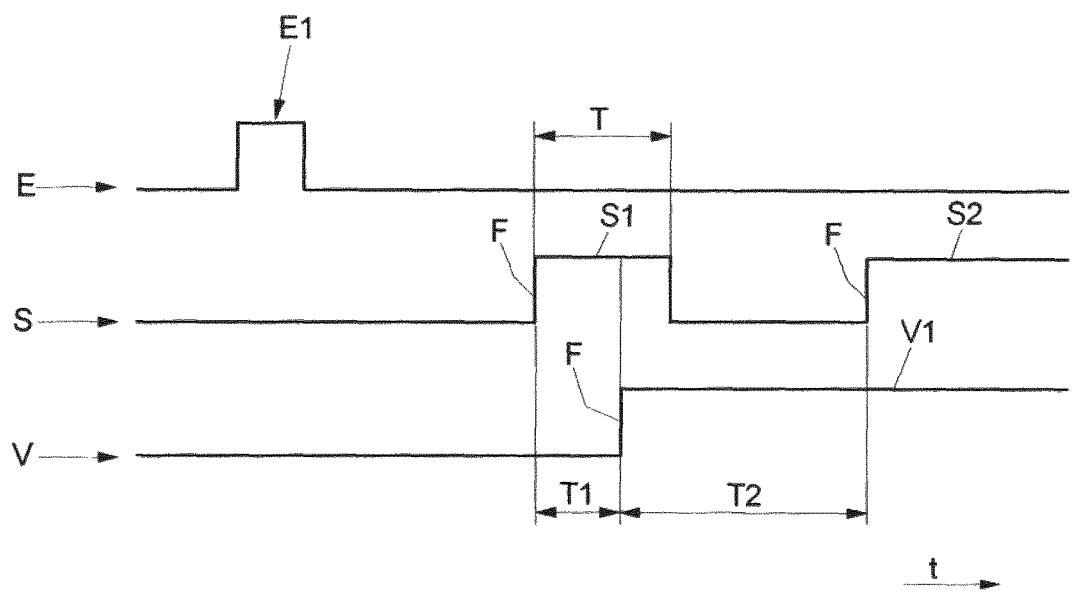
FIG. 4A, 4B show diagrams of time lines of visual alarm signals and audio alarm signals according to other embodiments of the invention.

FIG. 1 shows in a schematic drawing a scenario as it typically can be found in a hospital environment, for example in an intensive care unit of a hospital. Next to the bed B of a patient a number of infusion devices 20 constituted for example as infusion pumps, such as syringe pumps or volumetric pumps, are located and connected to a patient via infusion lines 21. The infusion devices 20 serve to administer a fluid such as a medication or nutrients contained in containers 5 via infusion lines 21 to the patient, the infusion lines 21 (especially in the environment of an intensive care unit of a hospital) possibly being vital to the patient such that they under all conditions must remain connected to the patient to ensure the required administration of medication, nutrients or the like.

Typically, the infusion devices 20 constituted as infusion pumps are organized on a rack 2 to form a vertical stack of infusion devices 20 which is fixed for example to a stand 4. The stand 4 may comprise wheels such that the stand 4 at least to some extend is movable with respect to the patient's bed B or together with the patient's bed B. The stand 4 may comprise a pole 40 to which the rack 2 for carrying the infusion devices 20 is attached and comprises, at its top end, fastening means in the shape of hooks to fasten a number of containers 5 containing medication or nutrients or other fluids to be administered to the patient.

The rack 2 serves to arrange the infusion devices 20 in an organized fashion at the bedside of the patient. The rack 2 herein provides a power supply for the infusion devices 20, ensures a secure and reliable fixation of the infusion devices 20, and provides a communication of the infusion devices 2 among each other and with an external communication network and with external periphery devices such as a nurse call, a printer, a computer, a monitor or the like.

Conventionally, the infusion devices 20 can be fixed to the rack 2 and for this are mechanically and electrically connected to the rack 2 such that via the rack 2 each infusion device 20 can be supplied with power and may communicate with other infusion devices 20 and with external devices and/or an external communication network. The rack 2 hence serves as a communication spine providing a communication facility and an electric power supply and embedding the infusion devices 20 into a hospital environment including a hospital communication network and a hospital management system.

As shown in FIG. 1, a multiplicity of different medical devices, namely infusion devices 20, a rack 2 and a central control device 3, may be arranged at the bedside B of a patient. The infusion devices 20 may for example be controlled by the central control device 3, also referred to as infusion manager and allowing a user, for example a nurse, to enter control commands relating to the different infusion devices 20 via a central terminal. The control device 3 for this purpose comprises a touch-sensitive display 30 allowing a user to enter control commands and displaying operational information relating to the infusion devices 20 to the user.

The control device 30 is connected to the rack 2 via a communication line 31 for transferring data signals between the control device 3, the rack 2 and the infusion devices 20 arranged on the rack 2. The control device 3 and/or the rack 2 may furthermore be connected to a hospital communication network and hence may be connected to external, additional control devices.

If an alarm condition occurs at one of the infusion devices 20, at the rack 2 or at the central control device 3, an alarm shall be initiated indicating to a user the occurrence of the alarm condition.

For this, each infusion device 20, as schematically shown in FIG. 2, may comprise a control unit 200, a visual alarm signal generator 201 and an audio alarm signal generator 202 for producing a visual alarm signal V and an audio alarm signal S, respectively.

The rack 2 and the central control unit 3 may likewise comprise a control unit, a visual alarm signal generator and an audio alarm signal generator such that alarm signals S, V may also be generated at the rack 2 and/or the central control device 3.

In particular in an environment as it can be found for example in an intensive care unit of a hospital, multiple medical devices 2, 3, 20 may operate in parallel and may issue sounds and a variety of different visual signals at the same time such that at any time a user perceives a large number of sensory inputs from the medical devices 2, 3, 20. In this regard, besides a system 1 comprising infusion devices 20 as shown in FIG. 1, other medical devices such as monitoring devices, for example a cardiac monitor, or life-sustaining equipment may be present and may produce audio and visual sensory signals during their operation.

The presence of various, ongoing audio and visual signals leads to a sensory pollution, which may make it difficult for a user to perceive a newly generated sensory signal such as an alarm signal upon its occurrence. The presence of multiple different signals may furthermore make it difficult for a user to identify the source of an alarm signal, even if the alarm signal is readily perceived by the user.

This general problem shall be improved by means of the instant solution in that, upon the occurrence of an alarm condition, an audio alarm signal and a visual alarm signal are produced at a medical device 2, 3, 20 in a concerted fashion. Herein, an audio alarm signal S and a visual alarm signal V are generated by means of the audio alarm signal generator 202 and the visual alarm signal generator 201 such that the alarm signals S, V are generated and issued having a predetermined time difference in between them. The audio alarm signal S and the visual alarm signal V hence are not generated at the same time, but are offset with respect to each other in a predetermined fashion.

As shown for example in FIG. 3, the triggering of alarm signals S, V is caused upon occurrence of an event E1 as shown in the event timeline E at the top of the diagram. Herein, upon occurrence of the event E1, alarm signals S1, V1 are generated by the visual alarm signal generator 201 and the audio alarm signal generator 202, as shown in the audio alarm signal timeline S and the visual alarm signal timeline V.

As depicted in FIG. 3, the audio alarm signal S1 and the visual alarm signal V1 are offset in time by a predetermined time difference T1. The time difference T1 is measured between the rising flanks F of the alarm signals S1, V1 and may be for example 50 ms. In the shown example, the visual alarm signal V1 herein precedes the audio alarm signal S1 by the predetermined time difference T1.

As illustrated in FIG. 3, the time difference T1 between the rising flanks F of the visual alarm signal V1 and the audio alarm signal S1 may lie in time intervals TL, TB. In particular, the visual alarm signal V1 may precede the audio alarm signal S1 by a time difference T1 lying in the time interval TL, denoted as "lead time interval". It however is also possible that the visual alarm signal V1 lags behind the audio alarm signal S1. In this case the time difference T1 lies in the time interval TB, denoted as "lag time interval". Hence, the rising flank F of the visual alarm signal V1 lags behind the rising flank of the audio alarm signal S1.

In general, the time difference T1 by which the visual alarm signal V1 precedes or lags behind the audio alarm signal S1 may be configurable by a user. According to the configuration setting the visual alarm signal V1 and the audio alarm signal S1 have a predetermined timing relationship, i.e., they are offset with regard to each other by the predetermined time difference T1.

The lead time interval TL may have a size of 100 ms. The time difference T1 by which the visual alarm signal V1 precedes the audio alarm signal S1 may for example lie in the range between 5 ms and 100 ms, preferably between 20 ms and 70 ms, for example at 50 ms.

The lag time interval TB may have a maximum size of 40 ms such that the visual alarm signal V1 may be set to lag behind the audio alarm signal S1 by at most 40 ms. The time difference T1 by which the visual alarm signal V1 lags behind the audio alarm signal S1 may for example lie on the range between 5 ms to 40 ms, for example at 30 ms.

The visual alarm signal V1 may be a steady light signal, for example caused by a light shining up. Just as well the visual alarm signal V1 may be a time-varying signal, for example caused by blinking light or by a time varying mark like a rectangular box displayed on a display of the medical device 2, 3, 20 in a blinking fashion.

The audio alarm signal S1 may be a steady sound at a single frequency or being formed by multiple discrete frequency components or having a specific frequency characteristic. The audio alarm signal S1 may also be a time-varying signal, such as a buzzing or beeping sound or a predefined melody.

The visual alarm signal V1 and/or the audio alarm signal S1 may last over a predetermined time period, or they may last until they are switched off by a user. Beneficially, the preceding alarm signal, in the case of FIG. 3 the visual alarm signal V1, at least lasts until the other alarm signal, in the case of FIG. 3 the audio alarm signal S1, occurs, such that the visual alarm signal V1 and the audio alarm signal S1 at least for some time coincide.

Figure 4B:
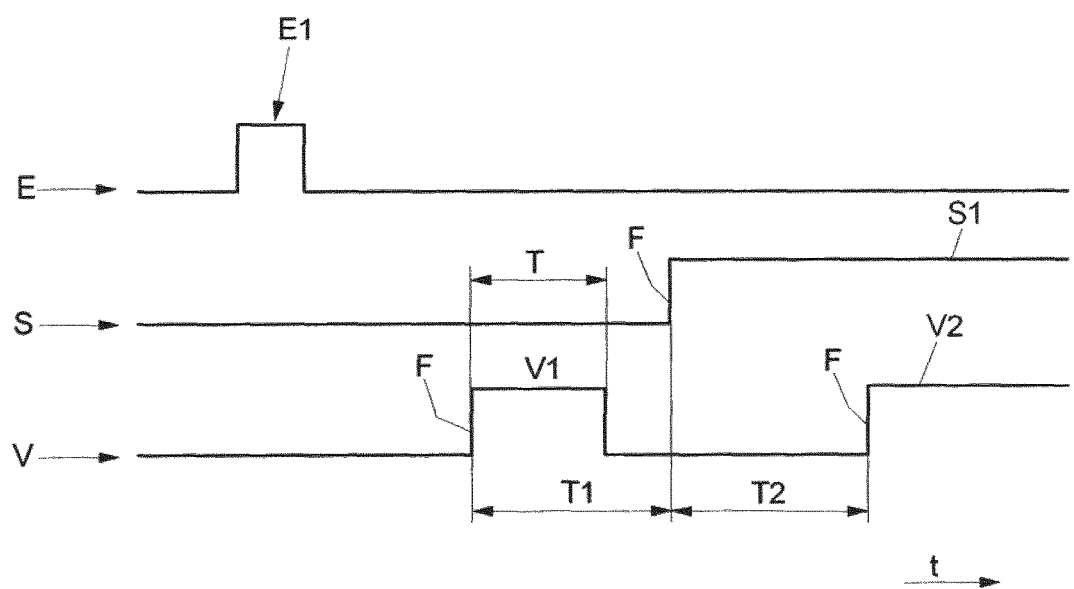

In principle, also more than one visual alarm signal V1, V2 and more than one audio alarm signal S1, S2 may be generated in a concerted fashion, as it is shown schematically in FIG. 4A and FIG. 4B.

In the example of FIG. 4A, upon occurrence of an event E1 a first audio alarm signal S1 is generated, preceding a visual alarm signal V1. In this case, the first audio alarm signal S1 lasts over a time period T (larger than the time difference T1 between the first audio alarm signal S1 and the visual alarm signal V1) and is switched of upon lapse of the time period T. After a predetermined time difference T2 after the rising flank F of the visual alarm signal V1, another, second audio alarm signal S2 is generated, which again may last over a predetermined time period T or which may last until a user switches it off.

In another example as shown in FIG. 4B, upon occurrence of an event E1 qualifying as an alarm condition, a first visual alarm signal V1 is generated, preceding an audio alarm signal S1 by a predetermined time difference T1. In this case the first visual alarm signal V1 is switched off after a time period T, and after the rising flank F of the audio alarm signal S1 another, second visual alarm signal V2 is generated, lagging behind the audio alarm signal S1 by a time difference T2.

As said, an alarm generation means as described herein may be provided not only in the infusion devices 20, but also within the rack 2 or the central control device 3.

In principle, it is not necessary that the visual alarm signal generator 201 and the audio alarm signal generator 202 are collocated within the unit of the medical device 2, 3, 20, for example on a housing of the medical device 2, 3, 20. In principle, for example the audio alarm signal generator 202 may also be separate from the physical unit of the medical device 2, 3, 20 and may for example be placed elsewhere in a modular fashion within a system of medical devices 2, 3, 20, but being in communication connection with the medical device 2, 3, 20.

The idea underlying the invention is not limited to the embodiments described above, but may be carried out in an entirely different fashion.

In principle, the instant invention is not limited to infusion devices as described herein, but may be implemented also in the context of entirely different medical devices.

Visual alarm signals may be any signals that may be visually perceived by a user. Audio alarm signals, in contrast, may be any alarm signals which may be audibly perceived by a user.

In particular, visual alarm signals may be generated by light components, display devices or other visual signal generation means. Audio alarm signals may be generated by any acoustic transducer, for example a piezoelectric transducer or an electromagnetic transducer, for example a loudspeaker.

LIST OF REFERENCE NUMERALS

1 System
2 Organization device

20 Infusion device
200 Control unit
201 Visual alarm generator
202 Audio alarm generator
21 Infusion lines
3 Control device (infusion manager)
30 Input device (touch-sensitive display)
31 Communication line
4 Stand
40 Pole
5 Infusion bags
B Patient's bed
E Event time line
E1 Event
F Rising flank
S, S1, S2 Audio alarm signal
t Time
T Time period
T1, T2 Time difference
TB Lag time interval
TL Lead time interval
V, V1, V2 Visual alarm signal

The invention claimed is:

1. A medical device, in particular medical infusion device, comprising:
   a control unit for controlling operation of the medical device,
   a visual alarm generator for generating a visual alarm signal, and
   an audio alarm generator for generating an audio alarm signal,
   wherein the control unit is configured to control the visual alarm generator and the audio alarm generator, in case of an alarm condition, for producing the visual alarm signal and the audio alarm signal which are offset with respect to each other by a predetermined time difference
   wherein the control unit is configured to control the visual alarm generator and the audio alarm generator, in case of the alarm condition, such that the visual alarm signal precedes the audio alarm signal by the predetermined time difference; and
   wherein the predetermined time difference is in a range between 5 ms and 100 ms.

2. The medical device according to claim 1, wherein the offset is measured between a rising flank of the visual alarm signal and a rising flank of the audio alarm signal.

3. The medical device according to claim 1, wherein the visual alarm generator comprises an LED component, an incandescent lamp, a vacuum display tube, a CRT display device, an LCD display device and/or an OLED display device.

4. The medical device according to claim 1, wherein the visual alarm generator is configured to produce a steady visual alarm signal or a time-varying visual alarm signal.

5. The medical device according to claim 1, wherein the audio alarm signal generator comprises an acoustic transducer such as a piezoelectric buzzer, an electromagnetic buzzer, and/or a loudspeaker.

6. The medical device according to claim 1, wherein the audio alarm signal generator is configured to produce a steady audio alarm signal or a time-varying audio alarm signal.

7. The medical device according to claim 1, wherein the predetermined time difference is in a range between 20 ms and 70 ms.

8. A medical device, in particular medical infusion device, comprising:
   a control unit for controlling operation of the medical device,
   a visual alarm generator for generating a visual alarm signal, and
   an audio alarm generator for generating an audio alarm signal,
   wherein the control unit is configured to control the visual alarm generator and the audio alarm generator, in case of an alarm condition, for producing the visual alarm signal and the audio alarm signal which are offset with respect to each other by a predetermined time difference,
   wherein the control unit is configured to control the visual alarm generator and the audio alarm generator, in case of the alarm condition, such that the audio alarm signal precedes the visual alarm signal by the predetermined time difference,
   wherein the predetermined time difference is in a range between 5 ms and 70 ms.

9. The medical device according to claim 8, wherein the predetermined time difference is in a range between 10 ms and 40 ms.

10. A medical device, in particular medical infusion device, comprising:
    a control unit for controlling operation of the medical device,
    a visual alarm generator for generating a visual alarm signal, and
    an audio alarm generator for generating an audio alarm signal,
    wherein the control unit is configured to control the visual alarm generator and the audio alarm generator, in case of an alarm condition, for producing the visual alarm signal and the audio alarm signal which are offset with respect to each other by a predetermined time difference
    wherein the control unit is configured to control the visual alarm generator and the audio alarm generator, in case of the alarm condition, to produce
    a first audio alarm signal,
    a first visual alarm signal following the first audio alarm signal by a first predetermined time difference, and
    a second audio alarm signal following the first visual alarm signal by a second predetermined time difference.

11. The medical device according to claim 10, wherein the first predetermined time difference is in a range between 5 ms and 40 ms, whereas the second predetermined time difference is in a range between 5 ms and 100 ms.

12. A medical device, in particular medical infusion device, comprising:
    a control unit for controlling operation of the medical device,
    a visual alarm generator for generating a visual alarm signal, and
    an audio alarm generator for generating an audio alarm signal,
    wherein the control unit is configured to control the visual alarm generator and the audio alarm generator, in case of an alarm condition, for producing the visual alarm signal and the audio alarm signal which are offset with respect to each other by a predetermined time difference wherein the control unit is configured to control the visual alarm generator and the audio alarm generator, in case of the alarm condition, to produce a first visual alarm signal, a first audio alarm signal following the first visual alarm signal by a first predetermined time difference, and a second visual alarm signal following the first audio alarm signal by a second predetermined time difference.

13. The medical device according to claim 12, wherein the first predetermined time difference is in a range between 5 ms and 100 ms, whereas the second predetermined time difference is in a range between 5 ms and 40 ms.

\* \* \* \* \*